(12) United States Patent
Rangabhatla et al.

(10) Patent No.: US 10,583,216 B2
(45) Date of Patent: Mar. 10, 2020

(54) SCAFFOLD COMPOSITIONS FOR TISSUE REPAIR

(71) Applicants: INNOVATIVE NANO & MICRO TECHNOLOGIES PVT LTD (INM TECHNOLOGIES), Bangalore (IN); SHILPA MEDICARE LIMITED, Raichur, Karnataka (IN)

(72) Inventors: Gunneswara Subramanya Vara Prasad Rangabhatla, Bangalore (IN); Sai Laxmi Aparna Rangabhatla, Bangalore (IN); Ratna Phani Ayalasomayajula, Bangalore (IN)

(73) Assignee: SHILPA MEDICARE LIMITED, Raichur, Karnataka ( * ) Notice: Subject to any disclaimer, the term of this patent is extended or adjusted under 35 U.S.C. 154(b) by 0 days.

(21) Appl. No.: 16/349,277

(22) PCT Filed: Dec. 12, 2017

(86) PCT No.: PCT/IB2017/057811
§ 371 (c)(1),
(2) Date: May 13, 2019

(87) PCT Pub. No.: WO2018/116052
PCT Pub. Date: Jun. 28, 2018

(65) Prior Publication Data
US 2019/0343983 A1 Nov. 14, 2019

(30) Foreign Application Priority Data
Dec. 20, 2016 (IN) .............................. 201641043431

(51) Int. Cl.
*A61L 26/00* (2006.01)
*A61K 31/195* (2006.01)
*A61K 33/06* (2006.01)
*A61P 7/04* (2006.01)

(52) U.S. Cl.
CPC ........ *A61L 26/0066* (2013.01); *A61K 31/195* (2013.01); *A61K 33/06* (2013.01); *A61L 26/0023* (2013.01); *A61L 26/0085* (2013.01); *A61P 7/04* (2018.01); *A61L 2300/102* (2013.01); *A61L 2300/21* (2013.01); *A61L 2300/418* (2013.01); *A61L 2430/12* (2013.01)

(58) Field of Classification Search
CPC ....... A61L 26/00; A61K 31/195; A61K 33/06; A61P 7/04
See application file for complete search history.

(56) References Cited

U.S. PATENT DOCUMENTS

| 7,371,403 B2 | 5/2008 | McCarthy et al. |
| 7,482,503 B2 | 1/2009 | Gregory et al. |
| 7,981,872 B2 | 7/2011 | Hardy et al. |
| 8,722,081 B2 | 5/2014 | Filatov et al. |
| 2007/0237877 A1 | 10/2007 | Diosady et al. |

FOREIGN PATENT DOCUMENTS

GB 2095995 B 10/1982

*Primary Examiner* — Zohreh A Fay

(57) ABSTRACT

The present invention relates to hemostatic scaffold compositions and the method of preparation thereof. In present invention, hemostatic scaffold compositions for wound care and dental care, uses chitosan and tranexamic acid.

2 Claims, 4 Drawing Sheets

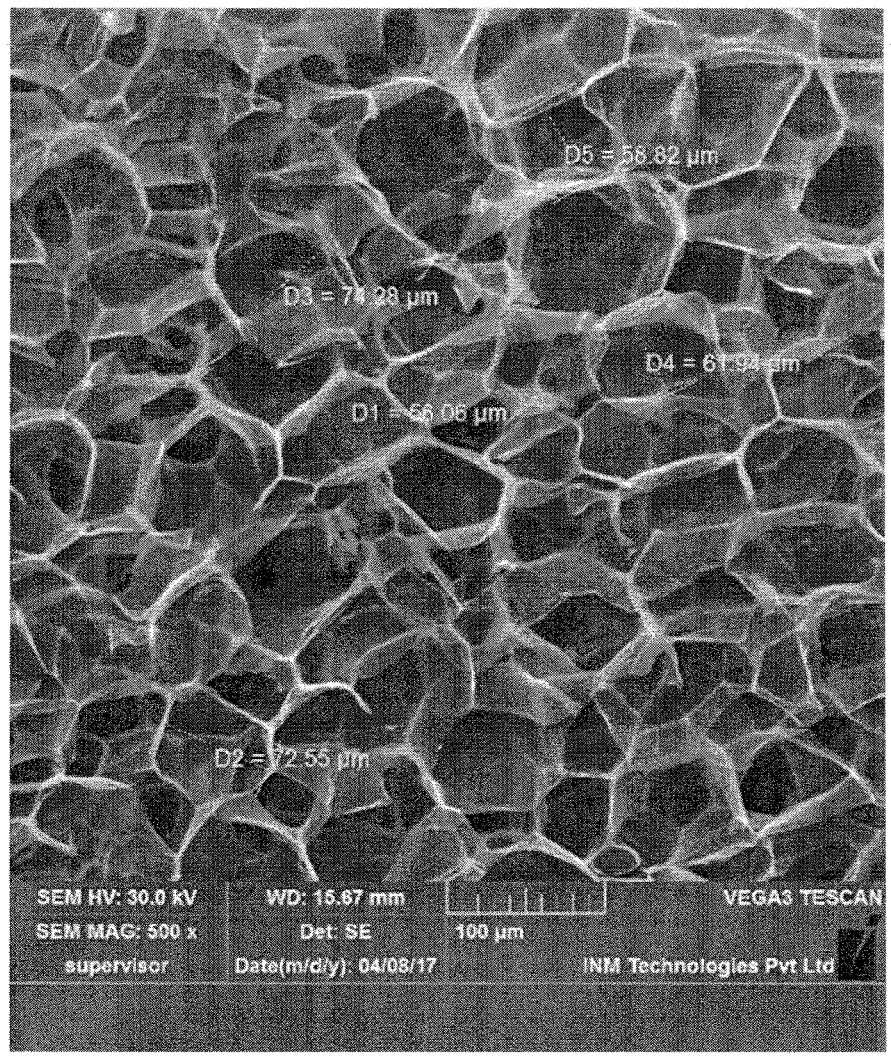
Figure 1: Scanning electron microscopy of centre part of the scaffold showing 50-70 μm pore size.

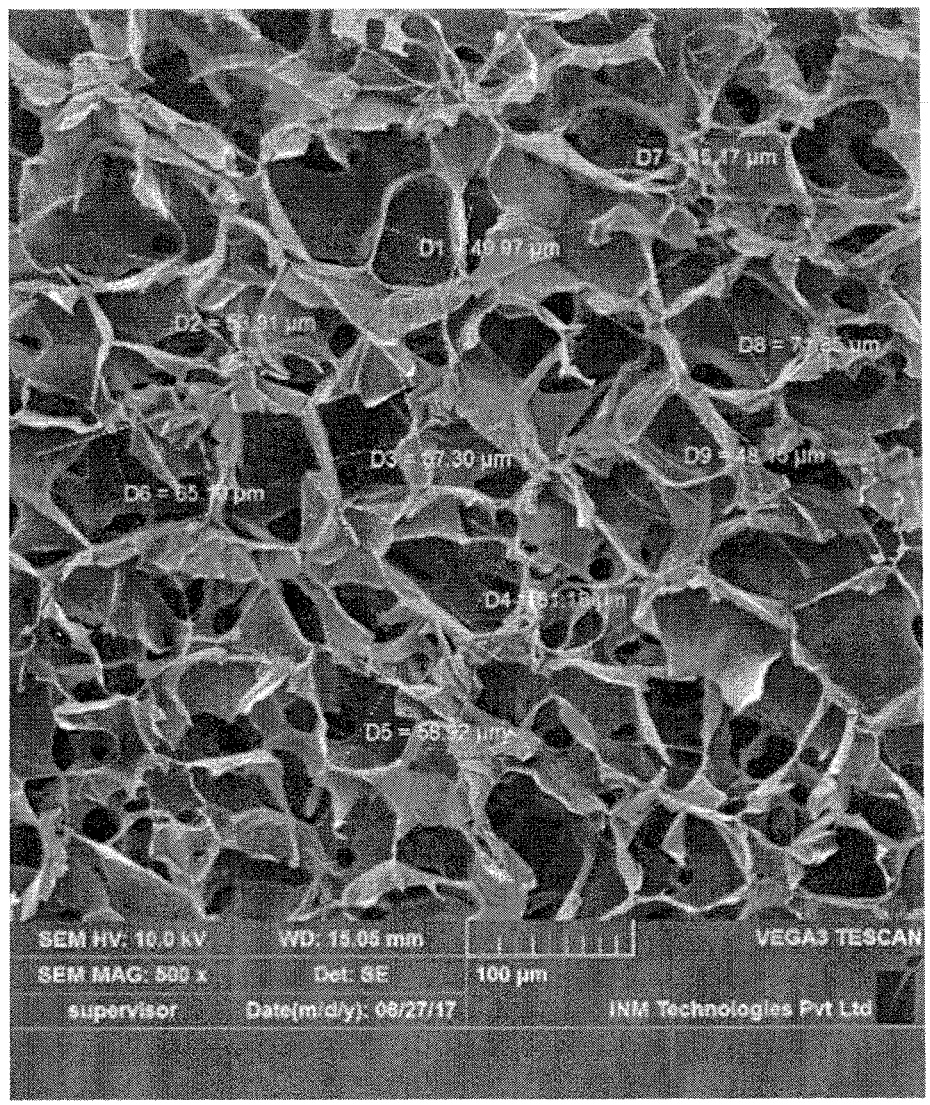
Figure 2: Scanning electron microscopy of cross section the scaffold showing 40-70 μm pore size.

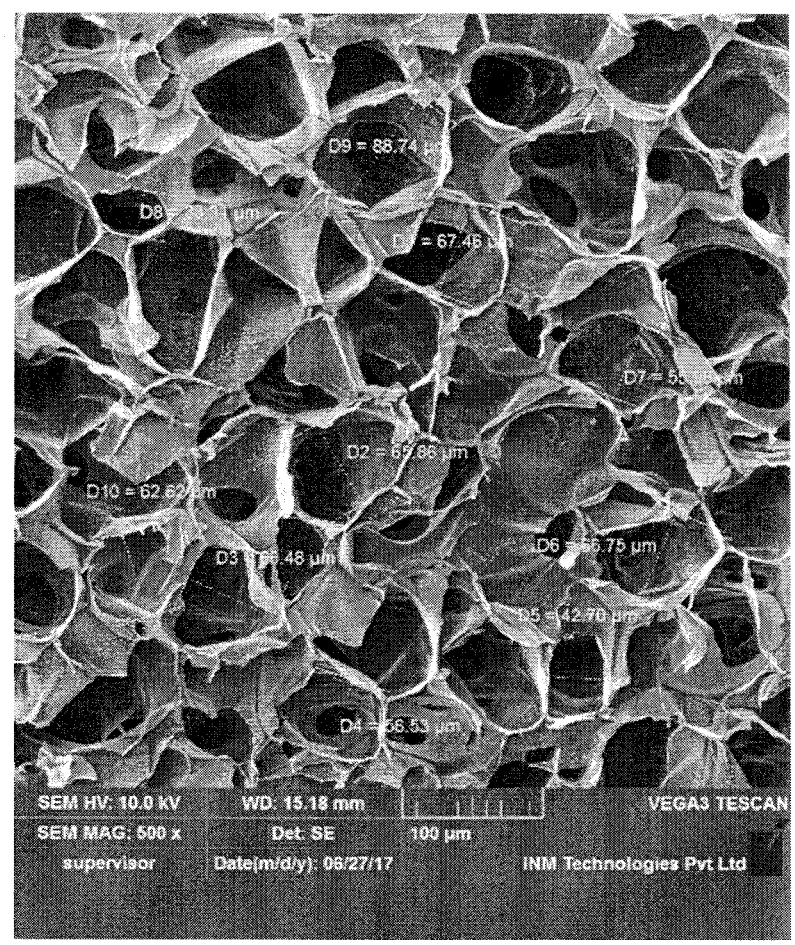
Figure 3: Scanning electron microscopy of side view the scaffold showing 40-60 μm pore size.

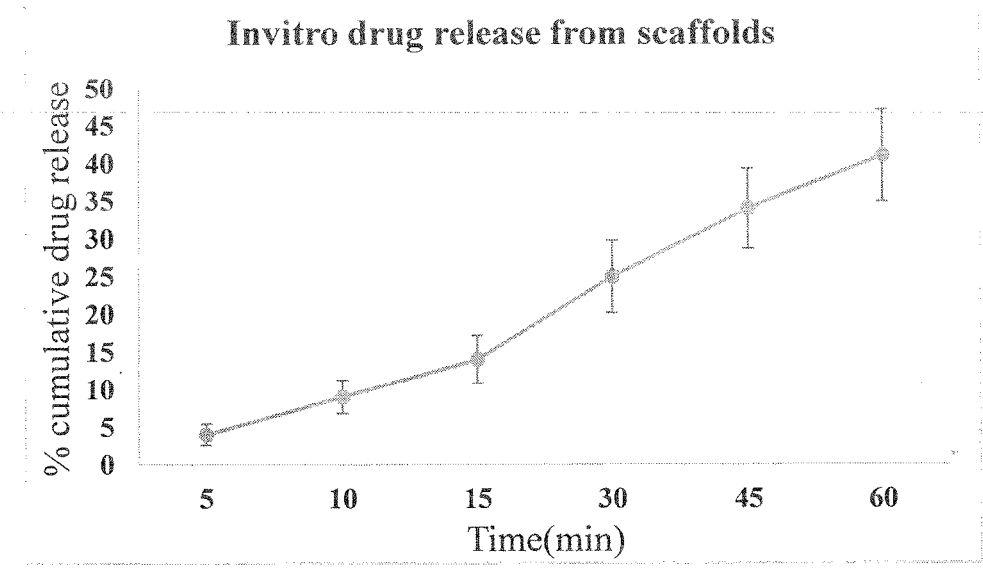
Figure 4: Invitro drug release of tranexamic acid from the scaffold in 7.4 PBS showing atleast 40% release in 60min.

SCAFFOLD COMPOSITIONS FOR TISSUE REPAIR

FIELD OF INVENTION

The invention relates to hemostatic scaffold compositions and the method of preparation thereof. In present invention, hemostatic scaffold compositions for wound care, especially for treatment of hemorrhage, burns, tissue regeneration uses chitosan and tranexamic acid. The present invention is further directed towards dental scaffold compositions comprising chitosan, tranexamic acid and nano dicalcium silicate for tissue repair and the methods applied during or after a dental procedure to ameliorate bleeding, fluid seepage or weeping, or other forms of fluid loss, as well as promote healing.

BACKGROUND OF THE INVENTION

Traditionally the primary technique adopted for stemming blood flow is the application of continuous pressure to the wound e.g. external wounds on body surface or dental wounds. This enables clotting factors to collect at the wound site and form a congealed blood mass to stem blood flow. However, this technique is not suitable for severe wounds and wounds having multiple bleeding points. Therefore, bleeding from the external wounds on body surface continues to be a major cause of death.

Death caused by bleeding out is a particular problem on the battle field. Typically wounds arising in this situation are accompanied by significant bleeding, and may result in death amongst the civilian population following trauma.

Several advancements have been made in the area of wound care in last few decades, however pre-hospital wound care and continuous wound care are stilled undeserved globally. Bleeding to death from traumatic injury is common in civilian and battle fields, which may or may not be accompanied with burns and other wounds that could be acute in nature.

Accident and trauma related injuries account for approximately 10% of deaths per year. Uncontrolled bleeding from wound site is a major cause of these preventable deaths. From a fatal wound approximately 40 ml/min of blood is lost and if it continues for 20 minutes, the victim dies of hemorrhagic shock. Bleeding to death before reaching medical facility is common to battle field injuries as well. Very often victims bleed to death due to lack of pre-hospital care, time and distance to reach a medical facility. Due to absence of external hemostatic products, the primary intervention to stop bleeding still remains to be cotton gauze using pressure. Lack of adequate pre-hospital care is stated as one of the prominent reasons of trauma related deaths.

Transportation of burn victims to the nearest medical facility is also a major unsolved issue. Due to this victim die of post injury infections which are preventable deaths. Though there is an unmet need in both the cases, it is pertinent to note that there is not even a single product which can stop bleeding quickly or to protect wounds until the victim reaches a medical facility.

At present the related products present in market are not made to address all these issues, but they have limited success to solve specific problems. The related products a product sold under the brand name QuickClot®. QuickClot® comprises a zeolite compound which absorbs water from blood flowing from a wound such that the clotting factors present in the blood become concentrated and the blood coagulates more quickly thereby the zeolite and the coagulated blood together form a coagulum to stem blood flow. After application of QuickClot® to the wound, zeolite absorbs water and QuickClot® generates heat, which reaches the temperature of 50° C. As it is necessary to apply constant pressure to the wound site following application of QuickClot® such temperatures make the application of pressure very difficult with medics needing to separate themselves from the wound site with any available material to prevent the discomfort accompanied with the heat generation. Furthermore, as the medic reaches for material to put between himself and the hot wound area he has to release the pressure. This can lead to channels appearing in the developing coagulum through which the blood can escape. If this happens then it is necessary to remove QuickClot® and start again. Ideally, a second person is required to ensure constant compression is applied. Other problems associated with QuickClot® also relate to heat generated upon contact with water. For example, as the product is a powder inevitably some settles on the skin surrounding the wound. If the skin is wet and heat generated can cause burns. Using QuickClot® in wet and windy weather is also problematic as it may cause discomfort or even burns to a person standing nearby.

Further during and after conventional dental procedures, e.g.; endodontic surgery, periodontal surgery, orthodontic treatment, tooth extractions, bleeding and fluid seepage typically occurs. Bleeding, fluid seepage or weeping, or other forms of fluid loss can also occur in the oral cavity as a result of injury or trauma to oral-maxillary tissue. Swelling and residual bleeding can be typically expected to persist during the healing period following the surgical procedure or injury. During the healing period, gum tissue regeneration occurs in the extraction sockets. It is thereby desirable during the healing period to take steps to stanch, seal, and/or stabilize the site of surgical intervention or the site of tissue injury or trauma against fluid loss due to bleeding, fluid seepage or weeping. During and after dental procedures or injury to the oral cavity, there is a need for quick and effective hemostasis.

Conventionally, absorbent cotton packs which are rolled or folded in the form of gauze pads are commonly used to stop the bleeding precipitated during and after dental procedures. While presence of such materials may absorb blood and body fluids which do not promote or create conditions conducive for rapid and long term hemostasis or healing.

Further products for control of bleedings from external wounds and dental wounds is described in U.S. Pat. No. 7,482,503 that comprises chitosan. The product is a sheet dressing comprising a chitosan layer. The dressing is applied to the site of the wound and forms a seal. The chitosan causes the blood to coagulate which together with the seal formed by the sheets stems the blood flow. However, such products must be applied directly to the source of bleeding i.e to an artery. Such application requires skill and accuracy. Military medics and first responders do not have the necessary skills to identify the source of bleeding and apply the dressing thereto. In any event, it would be extreme difficult to perform such a delicate operation on a battle field or at the trauma site.

GB2095995 discloses the use of pure chitosan acetate as a hemostatic material. However, the gel which forms from the pure salt is very thin as only the outermost surface of the material is available to act in a short period of time. Quite often this material fails to stop bleeding and even when it does, the clot is very thin and weak so that when the patient is moved, the clot compromised and bleeding resumes.

U.S. Pat. No. 7,371,403 relates to a wound dressing comprising a composite sponge comprising a freeze-dried and heat-compressed structure comprising chitosan biomaterial that stanches the blood flow at the wound site. The application of the heat may destroy the integrity of structure of biomaterial, which further fails to address the issue of batch to batch variability of chitosan that affects the end product, which is a major problem associated with natural polymers.

U.S. Pat. No. 7,981,872 relates to the hemostatic powder comprising a chitosan salt together with at least one medical surfactant.

US Patent Publication No. 20070237811 A1 describe a composition in which chitosan is prepared in a foamed gel that may be layered onto a suitable backing for use as a wound dressing, or the gel may be directly applied to wound, to affect hemostatic activity as a result of the chitosan.

U.S. Pat. No. 8,722,081 relates to hemostatic textile material to stop bleeding comprising: dialdehyde cellulose carrier, a selected component that prevents hemolysis; said component selected from the group consisting of tranexamic acid, and c-aminocaproic acid chemically immobilized thereon; and blood coagulation factor selected from the group consisting of chitosan and gelatin.

Therefore, it is an object of the invention to provide a hemostatic material which quickly stems the flow of blood from a wound and which is easy and safe to use.

According to the present invention there is provided a hemostatic material (scaffolds) comprising chitosan, tranexamic acid and an inorganic salt.

Advantageously, the hemostatic scaffold of the present invention can be applied by a person with only basic training. It is a matter of simply applying the scaffold to the wound area followed by pressure.

OBJECTS OF THE INVENTION

The main object of the invention is to provide multi-utility hemostatic scaffolds such as external wound scaffolds, dental scaffolds that can prevent hemorrhage, prevent microbial infections, protect burn wounds and also aid in tissue regeneration.

Another object of the invention is the hemostatic scaffold composition comprising chitosan and tranexamic acid.

A further object of the invention is the hemostatic scaffold composition comprising chitosan, tranexamic acid and an inorganic salt.

Another object of this invention is to maintain the structural integrity of the biomaterial by avoiding the usage of heat and employing the lyophilization process.

SUMMARY OF THE INVENTION

The present invention is directed to hemostatic scaffold composition such as external wound scaffolds, dental scaffolds that can prevent hemorrhage, prevent microbial infections, protect burn wounds and also aid in tissue regeneration.

Further the invention is directed to scaffold compositions applied during or after a dental procedure to ameliorate bleeding, fluid seepage or weeping, or other forms of fluid loss, as well as promote healing.

In embodiments of the invention, the hemostatic scaffold compositions of the present invention comprise a hydrophilic polymer. The hydrophilic polymer may be an alginate, chitosan (or its derivatives), a hydrophilic polyamine, polylysine, polyethylene imine, xanthan gum, carrageenan, Pectin, quaternary ammonium polymer, chondroitin sulfate, a starch, modified cellulosic polymer, dextran, hyaluronan or combinations thereof. Preferably, the hydrophilic polymer is chitosan.

In the embodiments of the invention the hemostatic scaffold composition may further comprise an active ingredient. The active ingredient may include, but not limited to an inorganic salts and tranexamic acid. Preferably the active ingredient is tranexamic acid and an inorganic salt.

In embodiments of the invention, the hemostatic scaffold composition comprises the inorganic salt as the active ingredient. The inorganic salts may be selected from the group consisting of hydroxyapatite, calcium sulphate, calcium silicate, calcium phosphate, magnesium silicate. Preferably the inorganic salt selected is dicalcium silicate. Dicalcium silicate with the particle size ranging from about 10 nm to about 500 nm is most preferably used dicalcium silicate (nano dicalcium silicate).

In another embodiment, a method of preventing severe bleeding in a subject comprising administering a hemostatic scaffold composition (for the external wounds) is provided, preferably, the subject is a mammal. More preferably, the mammal is human.

In the present invention chitosan, tranexamic acid, nano dicalcium silicate, acetic acid and deionized water are used. The process for producing the hemostatic scaffold comprises preparation of aqueous acetic acid solution, and addition of chitosan, tranexamic acid and nano dicalcium silicate into glacial acetic acid solution to form final solution or suspension. Further the final solution or suspension was subjected to lyophilization in specially designed metal moulds to produce a porous, flexible, interconnected scaffolds; and then cutting the stabilized end product, vacuum packing of it and finally sterilizing it by gamma irradiation.

In embodiments of the invention, the dental scaffold compositions of the present invention comprises a hydrophilic polymer. The hydrophilic polymer may be an alginate, chitosan (or its derivatives), a hydrophilic polyamine, polylysine, polyethylene imine, xanthan gum, carrageenan, Pectin, quaternary ammonium polymer, chondroitin sulfate, a starch, modified cellulosic polymer, dextran, hyaluronan or combinations thereof. Preferably, the hydrophilic polymer is chitosan.

The dental scaffold composition may further comprise an active ingredient. The active ingredient may include, but is not limited to an inorganic salts and tranexamic acid. Preferably the active ingredient is tranexamic acid and an inorganic salt.

In embodiments of the invention, the dental scaffold composition comprises the inorganic salt as the active ingredient. The inorganic salts may be selected from the group consisting of hydroxyapatite, calcium sulphate, dicalcium silicate, calcium phosphate, magnesium silicate. Preferably the inorganic salt selected is dicalcium silicate. Dicalcium silicate with the particle size ranging from about 10 nm to about 500 nm is most preferably used dicalcium silicate (nano dicalcium silicate).

In another embodiment, a method of preventing severe bleeding in a subject comprising administering a dental scaffold composition is provided, preferably, the subject is a mammal. More preferably, the mammal is human.

BRIEF DESCRIPTION OF DRAWINGS

FIG. 1: shows the image of center part of hemostatic scaffold under scanning electron microscope. The centre part of hemostatic scaffold has the pore size of about 50 μm to about 70 μm.

FIG. 2: shows the image of cross section of hemostatic scaffold under scanning electron microscope. The cross section of hemostatic scaffold has the pore size of about 40 µm to about 70 µm.

FIG. 3: shows the image of side view of hemostatic scaffold under scanning electron microscope. The side view of hemostatic scaffold has the pore size of about 40 µm to about 60 µm.

FIG. 4: shows the in vitro release of tranexamic acid from scaffold, showing that 40% of the tranexamic acid is released in sixty minutes' in pH 7.4 Phosphate buffer saline.

DETAILED DESCRIPTION OF THE INVENTION

The present invention is directed to hemostatic scaffold composition such as external wound scaffolds, dental scaffolds that can prevent hemorrhage, prevent microbial infections, protect burn wounds and also aid in tissue regeneration.

The present invention provides the hemostatic scaffold composition comprising the hydrophilic polymer and one or more active ingredients.

In one embodiment, the hemostatic scaffold compositions of the present invention comprise hydrophilic polymer. The hydrophilic polymer may be an alginate, chitosan (or its derivatives), a hydrophilic polyamine, polylysine, polyethylene imine, xanthan gum, carrageenan, Pectin, quaternary ammonium polymer, chondroitin sulfate, a starch, modified cellulosic polymer, dextran, hyaluronan or combinations thereof. Preferably, the hydrophilic polymer is chitosan. Chitosan is preferably used in the range from about 70% to about 80% of the total weight of scaffold composition.

In another embodiment, the hemostatic scaffold compositions of the present invention comprise chitosan and tranexamic acid. Tranexamic acid is preferably used in the range from about 15% to about 25% of the total weight of the scaffold composition.

In another embodiment the hemostatic scaffold compositions of the present invention comprise an active ingredient or combinations of active ingredients. The active ingredient may include, but is not limited to tranexamic acid and inorganic salts and combinations thereof.

In a further embodiment the hemostatic scaffold compositions of the present invention comprises an inorganic salt as the active ingredient. The inorganic salt may be selected from the group consisting of hydroxyapatite, calcium sulphate, dicalcium silicate, calcium phosphate, magnesium silicate. Preferably the inorganic salt selected is dicalcium silicate. Dicalcium silicate with the particle size ranging from about 10 nm to about 500 nm is most preferably used dicalcium silicate (nano dicalcium silicate). Nano dicalcium silicate is preferably used in the range from about 1% to about 5% based on the total weight of the scaffold composition.

In embodiments of the invention, tranexamic acid and the inorganic salts present in the hemostatic scaffold composition are in the ratio from about 1:100 to about 100:1. Preferably the ratio of tranexamic acid and the inorganic salts are present in the ratio from about 10:1 to 1:10.

In another embodiment, the present invention provides the hemostatic scaffold compositions consisting of chitosan, tranexamic acid and dicalcium silicate.

In another embodiment, the ratio of tranexamic acid to dicalcium silicate is present in the ratio of about 100:1 to about 1:100, preferably the ratio of tranexamic acid to dicalcium silicate is from about 10:1 to about 1:10.

In another embodiment, the present invention provides the hemostatic scaffold compositions consisting of chitosan, Tranexamic acid and nano dicalcium silicate, wherein the particle size of nano dicalcium silicate ranges from about 10 nm to about 500 nm.

In a further embodiment, the present invention provides the hemostatic scaffold composition consisting of about 70% to about 80% Chitosan, about 15% to about 25% of tranexamic acid and about 1% to about 5% of dicalcium silicate.

In another embodiment, the present invention provides the hemostatic scaffold composition consisting of about 70% to about 80% Chitosan, about 15% to about 25% of tranexamic acid and about 1% to about 5% of dicalcium silicate, wherein dicalcium silicate has the particle size of about 10 nm to about 500 nm.

In a specific embodiment, the present invention provides the hemostatic scaffold composition consisting of about 77% of chitosan, about 20% of tranexamic acid and about 4% of dicalcium silicate, wherein dicalcium silicate has the particle size of about 10 nm to about 500 nm.

The hemostatic scaffolds of the present invention have the pore size of about 30 µm to about 100 µm, and further on dissolution, at least 40% of tranexamic acid is released in about sixty minutes in Phosphate Buffer Saline of pH 7.4.

In embodiments of the invention, the present invention provides hemostatic scaffold composition consisting of about 70% to about 80% of chitosan, 15% to about 25% of tranexamic acid and about 1% to about 5% of dicalcium silicate, wherein dicalcium silicate has the particle size of about 10 nm to about 500 nm, and wherein the hemostatic scaffold has the pore size of about 30 µm to about 100 µm and wherein at least 40% of tranexamic acid is released in about sixty minutes in Phosphate Buffer Saline of pH 7.4.

In specific embodiments of the invention, the present invention provides hemostatic scaffold composition consisting of about 77% of chitosan, about 20% of tranexamic acid and about 4% of dicalcium silicate, wherein dicalcium silicate has the particle size of about 10 nm to about 500 nm, and wherein the hemostatic scaffold has the pore size of about 30 µm to about 100 µm and wherein at least 40% of tranexamic acid is released in about sixty minutes in Phosphate Buffer Saline of pH 7.4.

In the present invention, the process for preparation of hemostatic scaffold composition comprises the steps of
1. Water and acetic acid are mixed to form acetic acid solution in water
2. Chitosan solution or suspension is prepared by dissolving/dispersing the dry chitosan powder or flakes into acetic acid solution in water
3. Addition of tranexamic acid into the chitosan solution or suspension to form tranexamic acid and chitosan solution/suspension
4. To the tranexamic acid chitosan solution/suspension, nano dicalcium silicate was added to form final solution/suspension
5. Lyophilization (freeze drying)
   a. The suspension in step 3 is poured into trays
   b. Trays are loaded to the lyophilization chamber
   c. Then the suspension is passed through lyophilizing cycle
6. Stabilized end products are individually packaged in laminated metal pouches, which are vacuum sealed.
7. Individually packed final products are then terminally sterilized using gamma irradiation.

The present invention is directed to dental scaffold compositions applied during or after a dental procedure to ameliorate bleeding, fluid seepage or weeping, or other forms of fluid loss, as well as promote healing.

The present invention provides the dental scaffold composition comprising the hydrophilic polymer and one or more active ingredients.

In one embodiment, the dental scaffold compositions of the present invention comprise hydrophilic polymer. The hydrophilic polymer may be an alginate, chitosan (or its derivatives), a hydrophilic polyamine, polylysine, polyethylene imine, xanthan gum, carrageenan, Pectin, quaternary ammonium polymer, chondroitin sulfate, a starch, modified cellulosic polymer, dextran, hyaluronan or combinations thereof. Preferably, the hydrophilic polymer is chitosan.

The present invention provides the dental scaffold composition comprising the hydrophilic polymer and tranexamic acid.

In another embodiment the dental scaffold compositions of the present invention comprise an active ingredient or combinations of active ingredients. The active ingredient may include, but is not limited to tranexamic acid and inorganic salts and combinations thereof.

In a further embodiment the dental scaffold compositions of the present invention comprises an inorganic salt as the active ingredient. The inorganic salt may be selected from the group consisting of hydroxyapatite, calcium sulphate, calcium silicate, calcium phosphate, magnesium silicate. Preferably the inorganic salt selected is dicalcium silicate. The nano dicalcium silicate with the particle size ranging from about 10 nm to about 500 nm is most preferably used dicalcium silicate.

In the embodiments of the invention, tranexamic acid and the inorganic salts is present the dental scaffold composition in the ratio from about 1:100 to about 100:1. Preferably the ratio of Tranexamic acid and the inorganic salts is present in the ratio from about 10:1 to 1:10.

In another embodiment, the present invention provides the dental scaffold compositions consisting of chitosan, tranexamic acid and dicalcium silicate.

In the specific embodiment, the ratio of tranexamic acid to dicalcium silicate is present in the ratio of about 100:1 to about 1:100, preferably the ratio of Tranexamic acid to dicalcium silicate is present in the ratio from about 10:1 to about 1:10.

In another embodiment, the present invention provides the process for the preparation of dental scaffold compositions comprising the steps of
1. Dissolving/dispersing the hydrophilic polymer in a solvent to make the solution/suspension.
2. Addition of active ingredient to the hydrophilic polymer suspension/solution of step 1.
3. Addition of nano dicalcium silicate to the solution/suspension of step 1, mix and
4. freeze drying.

The solvent used to dissolve the hydrophilic polymer is selected from the group consisting of acetic acid, hydrochloric acid, lactic acid. The most preferably used solvent is acetic acid.

In the most preferred embodiment, the present invention provides the process for the preparation of dental scaffold compositions comprising the steps of
1. Mixing of acetic acid and water to form the acetic acid solution in water
2. Dissolving/dispersing the chitosan in acetic acid solution in water to make the chitosan solution/suspension
3. Addition of tranexamic acid to contents of step 2 to form chitosan and tranexamic acid solution/suspension 4. Addition of nano dicalcium silicate to contents of step 3 to form final solution/suspension
5. freeze drying or lyophilization.

In another embodiment, a method of preventing severe bleeding in a subject comprising administering a dental scaffold composition of the present invention is provided, preferably, the subject is a mammal. More preferably, the mammal is human.

In another embodiment this invention is used as a hemorrhage control for preparation of wound dressings (external wound scaffolds). The wound dressing (external wound scaffolds) for controlling severe bleeding is formed from chitosan, nano dicalcium silicate and Tranexamic acid. The wound dressing (external wound scaffolds) is being capable of substantially stanching the flow of the severe life-threatening bleeding from the wound by adhering to the wound site, to seal the wound, to accelerate blood clot formation at the wound site, to reinforce clot formation at the wound site and prevent bleed out from the wound site, and to substantially prohibit the flow of blood out of the wound site.

The size of the scaffold may range between 1 cm×1 cm to 5 cm×5 cm depending on the site of application. Lowest dimensions of scaffolds can be used to control the bleeding in oral cavity after dental procedures while larger scaffolds could be used for controlling bleeding of external wounds. However, size does not limit the property of the scaffold, any desirable size can be used depending on the site of application.

The following examples are provided to illustrate the present invention. It should be understood, however, that the invention is not limited to the specific conditions or details described in the examples below. The Examples should not be construed as limiting the invention as the examples merely provide specific methodology useful in the understanding and practice of the invention and its various aspects. While certain preferred and alternative embodiments of the invention have been set forth for purposes of disclosing the invention, modification to the disclosed embodiments can occur to those who are skilled in the art.

Example 1: Compositions and Preparation of Dental Scaffolds 2 gms of chitosan was dispersed in 97.4 gms of 0.5% w/v of acetic acid solution in water and stirred continuously until chitosan is dissolved/dispersed. While the aqueous chitosan solution/suspension was being stirred, 0.5 gms of tranexamic acid, was dissolved/dispersed into it. This was followed by the addition of 0.1 gm of nano dicalcium silicate. The suspension/solution was stirred. The resultant suspension/solution was further subjected to lyophilization process. The resultant lyophilized scaffold can be cut to different sizes and/or shapes, as desired. For example, a scaffold of diameter 2.2 cm and thickness of 0.4 cm, weighs 0.03 gm.

Example 2: Clotting Time of the Blood, Comparison of the Present Invention, with the Other Compositions

TABLE 1

| Dental Scaffold compositions | Clotting time |
| --- | --- |
| Control (only blood) | 7 min 11 sec |
| Chitosan scaffold composition | 6 min |

TABLE 1-continued

| Dental Scaffold compositions | Clotting time |
| --- | --- |
| Chitosan + nano dicalcium silicate (0.1%) scaffold composition | 5 min 26 sec |
| Chitosan + Tranexamic acid (0.5%) scaffold composition | 5 min |
| Chitosan + Tranexamic acid + nano dicalcium silicate dental scaffold composition as per example-1 | 1 min 03 sec |

From the table-1; dental compositions of the present invention prepared as per the example-1 has the less clotting time of blood when compared to the other compositions.

Example 3: Compositions and Preparation of Scaffolds for External Wounds 2 gms of chitosan was dissolved/dispersed in 97.4 gms of 0.5% w/v of acetic acid solution in water and stirred continuously until chitosan is dissolved/dispersed. While the aqueous chitosan solution/suspension was being stirred, 0.5 gms of tranexamic acid, was dissolved/dispersed into it. This was followed by the addition of 0.1 gm of nano dicalcium silicate. The suspension/solution was stirred. The resultant suspension/solution was further subjected to lyophilization process. The resultant lyophilized scaffold can be cut to different sizes and/or shapes, as desired. For example, a scaffold of diameter of 6.5 cm and thickness of 1.2 cm, weighs at 1 gm. The scaffold as cut is then sterilized. Dimensions of the scaffold could be of any size and shape based on the need.

Example 4: Pore Size of Scaffolds

Pore size of the scaffolds was measured by vega-3 software at different locations. Pore size of the scaffolds is important for infiltration of RBC into the scaffolds and helps in plate aggregation which will enhance the clotting ability of the scaffolds. The pore size distribution pattern of pores in the scaffold affect the water absorption and water vapor permeability of the scaffold. The scaffold of the example 3 have the pore size ranging from 30-100 µm. Different views of scanning electron microscope images are present in FIGS. 1, 2 & 3.

Example 5: Swelling Property

Swelling property of scaffold is estimated by using water. Initially 30 mg of the scaffold was incubated in water and wet weight of scaffolds were evaluated at two different time points (5 and 10 min). Swelling index was calculated by using the following formula $$Ww-Wo/Wo \times 100$$

Swelling index of the scaffolds was in the range of 100-8000 times of its initial weight.

Example 6: In Vitro Drug Release

In vitro drug release from the scaffolds was evaluated by modified method. Each scaffold was placed in 6 well cell culture plate and 5 ml of PBS (Phosphate Buffer Saline pH 7.4) was added to the each well. The total system was kept in orbital shaker at 50 rpm and samples were withdrawn at regular time intervals and subjected to HPLC analysis. Release of tranexamic acid was found to be 40% from the scaffold (example-3) in sixty minutes. The release of tranexamic acid is shown in figure

The invention claimed is:

1. A hemostatic scaffold composition consisting of about 70% to about 80% of chitosan, 15% to about 25% of tranexamic acid, and about 1% to about 5% of dicalcium silicate, wherein dicalcium silicate has the particle size of about 10 nm to about 500 nm.

2. A hemostatic scaffold composition consisting of about 70% to about 80% of chitosan, 15% to about 25% of tranexamic acid and about 1% to about 5% of dicalcium silicate, wherein dicalcium silicate has the particle size of about 10 nm to about 500 nm, and wherein the hemostatic scaffold has the pore size of about 30 µm to about 100 µm and wherein at least 40% of tranexamic acid is released in about sixty minutes in Phosphate Buffer Saline of pH 7.4.

* * * * *